United States Patent [19]

Wonder et al.

[11] Patent Number: 5,072,738
[45] Date of Patent: Dec. 17, 1991

[54] APPARATUS FOR PROTECTION A WOUND

[75] Inventors: Terry M. Wonder, Holladay; Joseph T. Sorenson, Murray; Garlyn W. Hendry; Lawrence A. Neer, both of Salt Lake, all of Utah

[73] Assignee: Sorex Medical, A Division of Sorenson Development, Inc., Salt Lake City, Utah

[21] Appl. No.: 585,038

[22] Filed: Sep. 17, 1990

Related U.S. Application Data

[63] Continuation of Ser. No. 339,208, Apr. 14, 1989, abandoned.

[51] Int. Cl.⁵ .............................................. A61F 13/00
[52] U.S. Cl. .................... 128/888; 128/157; 128/163; 128/846; 2/16; 606/215
[58] Field of Search ............... 128/155, 157, 163, 846, 128/858, 888, 890, 892; 2/15, 16, 22; 606/215, 216, 217, 218, 221

[56]        References Cited
       U.S. PATENT DOCUMENTS

| 1,290,141 | 1/1919 | Elleby . | |
| 2,254,669 | 9/1941 | Turner . | |
| 3,141,459 | 7/1946 | Orcutt . | |
| 3,304,938 | 2/1967 | Perkins, Jr. | 128/888 |
| 3,503,392 | 3/1970 | Beeman . | |
| 3,815,152 | 6/1974 | Bednarczuk et al. . | |
| 3,976,066 | 8/1976 | McCartney | 128/892 |
| 4,263,906 | 4/1981 | Finley | 128/157 |
| 4,905,681 | 3/1990 | Glascock | 128/155 |

FOREIGN PATENT DOCUMENTS

| 165664 | 10/1955 | Australia . | |
| 0902613 | 9/1945 | France | 128/888 |
| 8904157 | 5/1989 | PCT Int'l Appl. | 128/157 |

Primary Examiner—Randall L. Green
Assistant Examiner—Paul Prebilic
Attorney, Agent, or Firm—Trask, Britt & Rossa

[57]            ABSTRACT

A ventilated skin guard apparatus for protecting areas of sensitive skin is disclosed. The apparatus has two longitudinal end support members to which are connected a series of laterally placed arcuate members. Single arcuate members may be removed from the apparatus without removing the entire apparatus from the portion of the user's body having the sensitive area of skin.

22 Claims, 4 Drawing Sheets

APPARATUS FOR PROTECTION A WOUND

This application is a continuation of application Ser. No. 339,208, filed Apr. 14, 1989 now abandoned.

Related Application: This application is related U.S. Ser. No. 115,370 to Glascock licensed to the assignee of this application.

BACKGROUND OF THE INVENTION

1. Field:

This invention relates to an apparatus for protecting areas of sensitive skin. It is particularly directed to improved structure for protecting skin graft donor sites and burned skin sites from contact with clothing, bedding, and other objects.

2. State of the Art:

Other patents concerning this same general subject area include:

U.S. Pat. No. 1,290,140 (Elleby) discloses a protective face mask to be worn when milking cows. The face mask includes a padded frame with supporting wires that fit around the face, mask supporting wires fitted over a nonflexible mask wire netting, and an attached strap with fastening means.

U.S. Pat. No. 2,254,669 (Turner) discloses an eyeglass protector to be worn by a basketball or volleyball player. This invention includes a head harness made up of adjustable head bands with attached U-shaped wire loops, a front wire member frictionally engaged at the top of the headband, and an adjustable elastic chin strap.

Australian Patent No. 165,664 (The Scholl Manufacturing Company Limited), discloses an implement for apply tubular bandages to parts of the human or animal body. This implement includes a number of longitudinal members joined together at both ends by members having a central aperture which form a cage around the limb and can be transferred lengthwise onto the limb.

U.S. Pat. No. 3,503,392 (Beeman) discloses a support for maintaining dressings in a spaced relationship to wound or affected area of the body. This support includes a band of flexible material having a plurality of lateral extensions or fingers.

U.S. Pat. No. 3,815,152 (Bednarczuk et al.) discloses a protective football player's helmet. This disclosure consists of a rigid helmet portion with a recess, a removable secured chin strap, and a releasable face guard assembly.

U.S. Pat. No. 3,141,459 (Orcutt) discloses a device for use in supporting circumferential head bandages. This device consists of at least two flexible, rectangularly shaped head bandage support members which are pivotally connected to one or more similar members, and are approximately 180 degrees from each other with the center being at the top of the head.

SUMMARY OF THE INVENTION

The present invention includes a ventilated skin guard apparatus for protecting an area of sensitive or damaged skin (a "wound") on an injured portion of a person's body ("body portion"). The apparatus includes (a) support members for placement near the periphery of the wound; b) a flexible structure for limiting separation of the support members once placed about the wound which also surrounds the wound and conforms to the contour of the particular body portion having the wound; c) a plurality of lateral members arched over the wound to protect it from contact with foreign objects, the lateral members being adapted to grasp or otherwise connect with the end support members; and d) straps or other means adapted to connect with the lateral members to affix the lateral members and connected support members to the body portion. A notable characteristic of the assembled apparatus is the provision of apertures between the lateral cage members to allow ventilation of the damaged skin area while still protecting the area from contact with foreign objects.

The invention also includes resilient lateral or "cage" members which are arcuate or bowed. They are generally elongate frame pieces of a length selected to bridge the wound. At least one end of each cage member includes reliable fastening means. Typically this fastening means is fashioned on a tensioned jaw-like grasping portion for selectively connecting and releasing a support member. Either connection or release of the end support member may be accomplished while the apparatus is mounted to the user. Moreover, individual cage members may be rotated about an end support member once connected. Such rotation and easy removal allows for convenient access to the wound area without the need for removing the entire apparatus. The cage members may also be moved along the length of the support members while the apparatus is in use to afford greater protection of the wound area.

The cage members constitute springs which are inherently biased to a relaxed position in which the members have a relaxed effective length. In use, however, the ends of the cage members are attached to a pair of support members whose separation is defined by a cloth or strap connecting the two members. This separation is less than the relaxed effective length of the cage members, which is considered to be the linear distance between the opposing ends. somewhat compressed between the two support members. They thus exert spring pressure tending to separate the support members while the connection means keeps them together. Each cage member thus forms an arch above the wound. The arch provides relatively great strength to the cage members and protects the underlying area of skin from contact with foreign objects.

The smaller the width or lateral size of the wound, the more the cage members arch. Thus, the same cage members can be used to protect wounds of varying widths. Only the distance between the end support members need be adjusted. Such features allow for easy assembly and disassembly of the skin guard apparatus. The cage members may also be interchanged between different apparatus.

The apparatus may be used according to the following steps. First, the length of the support members is chosen to accommodate the length of the wound and to define generally its longitudinal borders. Second, the support members are linked to one another through the use of a fabric or other suitable structure which can define the area of the sensitive skin laterally. Third, this portion of the apparatus is laid about the periphery of the area of the wound. Fourth, the lateral cage members are connected to the support members to provide a protective arch over the wound. Alternatively, the third and fourth steps may be interchanged. Fifth, the straps or other affixation means are attached to the patient by affixing the apparatus about the area of sensitive skin, preferably without contacting any portion of the apparatus with the area of sensitive skin.

Optionally, an absorbent pad having an aperture of a size greater than that of the area of sensitive skin may be placed between the apparatus and the user. This foam pad may have an adhesive side for affixing to the apparatus or the user and may further be disposable.

The apparatus prevents foreign objects from contacting the sensitive area of skin which prevents pain and additional trauma to the skin. The apparatus thus may facilitate healing of the skin.

DESCRIPTION OF THE ILLUSTRATED EMBODIMENTS

Figure 1:
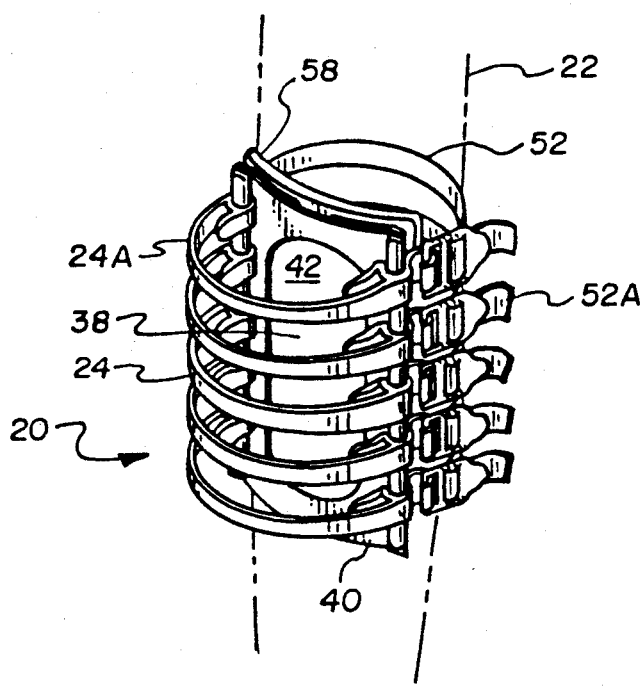
FIG. 1 depicts a skin guard apparatus according to the present invention affixed to a human limb (in phantom).

Referring to FIG. 1, a skin guard apparatus according to the present invention, generally 20, protects an area of sensitive skin. As depicted in FIG. 1, the apparatus may be attached to the body of the user around, for example, a limb 22 (shown in phantom) having the area of sensitive skin or wound.

Figure 2:
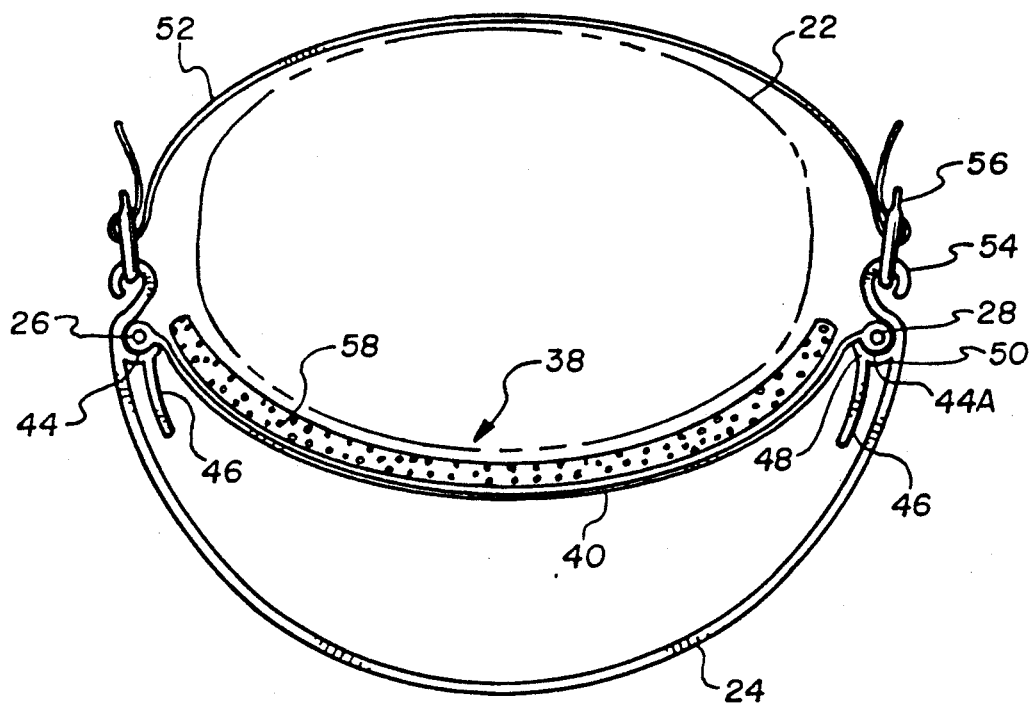
FIG. 2 depicts a cut-away top view of a skin guard apparatus according to the present invention affixed to a human limb (in phantom) with an absorbent foam pad placed between the apparatus and the limb.

The depicted apparatus includes multiple lateral or cage members 24, 24A connected to two longitudinal support members 26, 28. The cage members are bowed or arched to protect the area of sensitive skin. (FIGS. 1 & 2).

The support members may be sturdy rods or other framework which the lateral members can be connected. The length of the support members will generally vary with the length of the wound, with longer wound areas requiring longer end support members. The support members are generally placed on both sides of the periphery of the wound in a parallel or near parallel fashion.

Figure 3:
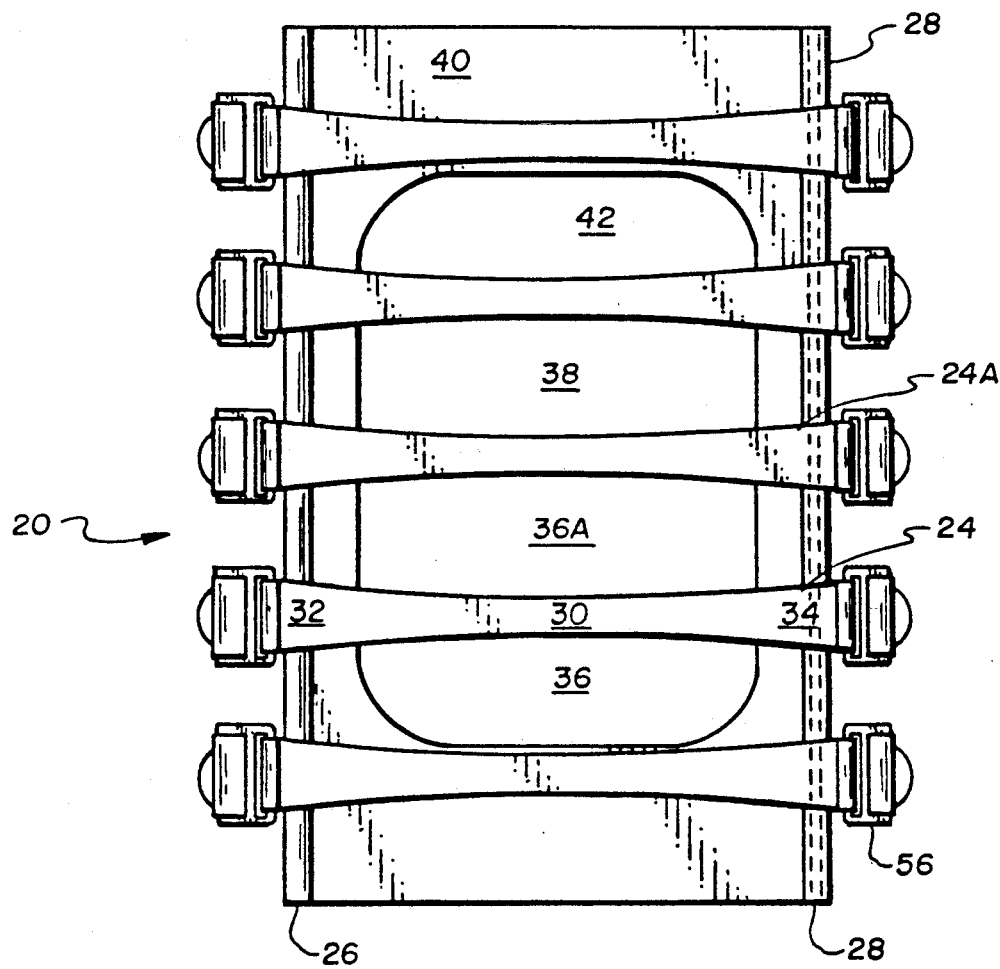
FIG. 3 depicts a frontal view of a skin guard apparatus according to the present invention.

The depicted cage members 24, 24A are typically made of a durable conformable material such as a plastic. As shown in FIG. 3, the width of the cage members may be narrower at the center (e.g., 1 centimeter (cm)) generally 30, than at the ends 32, 34 (e.g. 1.5 cm). This inward tapering increases the size of apertures 36, 36A between the cage members 24, 24A connected to the longitudinally placed end support members 26, 18. These apertures 36, 36A allow air to ventilate through the cage members 24, 24A and also allow for the spray application of various topical agents (e.g. antiseptics and anesthetics) to the sensitive area of skin 38 without removing a cage member 24 from the rest of the apparatus 20.

Alternatively, the width of the cage members can be narrower at the ends than at the center (not shown). This outward tapering can likewise increase the size of the apertures between the cage members allowing air ventilation and spray application of topical agents, with the further advantage of better protection of a wound from contact with clothing, bedding, or other objects.

A cage member may also have means adapted to connect with a strap 52 or other means to affix the cage member and any connected support member around the body portion having the area of sensitive skin. The connection means will typically be a hook 54 or loop-like arrangement, although any means of connecting the cage member to the strap or other structure will suffice so long as the components of the apparatus remain interconnected for as long as desired by the user.

Figure 6:
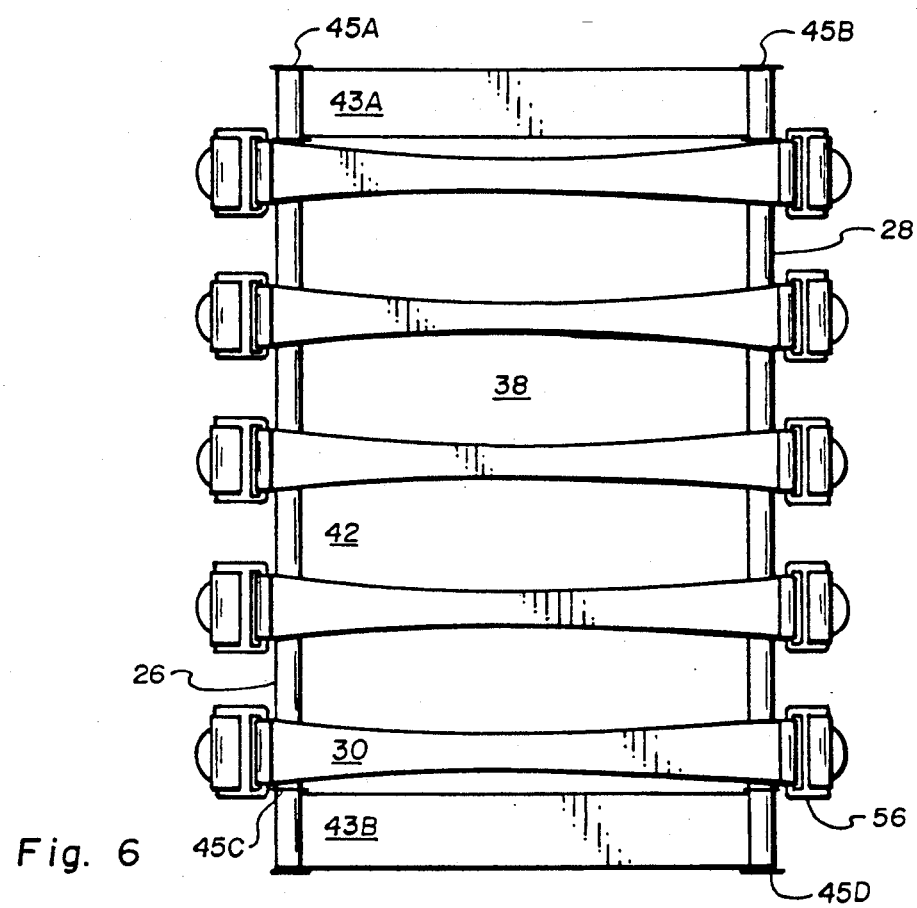
FIG. 6 depicts a frontal view of a skin guard apparatus according to the present invention wherein the connection means is a pair of straps wrapped about the end support members.

Cloth 40 (FIG. 3) or other structure, preferably flexible, is utilized in the apparatus to assist in maintaining the position of the support members once placed. This retaining structure is generally connected to both ends of each support member 26, 28 connecting them one to another, generally defining the area of sensitive skin. In its simplest embodiment, this structure can be lengths of string tied to the ends of each support member with the string defining the upper and lower borders of the area of sensitive skin, preferably without contacting it. (not shown) Preferably, straps 43A, 43B (FIG. 6), net, a piece or pieces of cloth or other flexible or contoured material may be used to maintain the positioning of the support members. Alternatively, a rigid or semi-rigid thermally conformable lateral retaining structure may be used to connect the support members.

Figure 4:
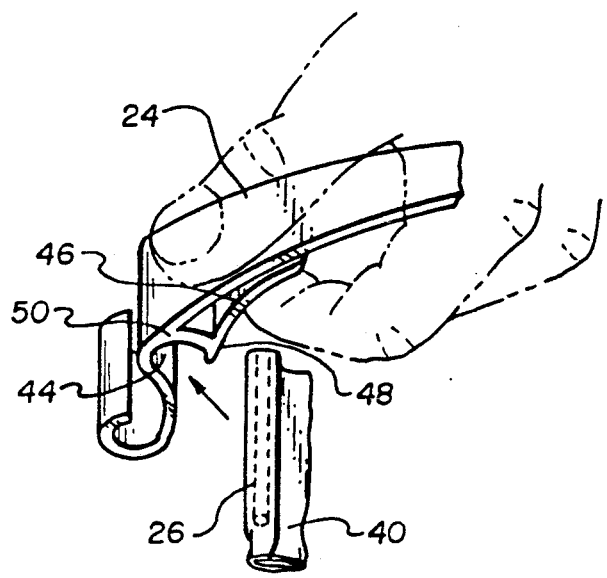
FIG. 4 depicts a cage member of the present invention, the grasping jaws of which are being opened by a hand (in phantom) to grasp a support member which has been wrapped with fabric.

The illustrated longitudinal support members 26, 28 (in phantom—FIG. 3) are associated with one another by a fabric 40 for maintaining the relative positioning of the support members 26, 28. The support members are preferably steel, metallic, or hard plastic rods having a length longer than that of the are of sensitive skin. In one depicted embodiment, the fabric 40 is wrapped about the support members 26, 28 and contains them (FIGS. 2, 3, & 4). Once wrapped, the fabric 40 may be sewn to form a seam or otherwise connected (e.g. with VELCRO hook and loop attachments) to itself to encase the support members 26, 28.

The fabric 40 may be cotton or other absorbent material and has an aperture 42 cut or formed therein, preferably sized to surround the periphery of the area of sensitive skin 38.

In one embodiment (FIG. 6), the aperture is defined on its sides by the support members 26, 28, and on the top and bottom by two laterally placed strips 43A, 43B of fabric which are wrapped about and sewn to encase the end support members. Spool-like end pieces 45A, 45B, 45C, 45D may be placed on the ends of support members 26, 28 for the fabric strips to be wrapped about.

Use of fabric 40 in the apparatus 20 is ideal. Fabric allows for the apparatus 20 to conform generally to the shape of the user's body portion 22 to which the apparatus 20 is affixed (FIG. 2). Fabric also allows some air to ventilate the portion of the user's body covered with the fabric. It is also absorbent and may be cleaned with standard detergent.

Figure 5:
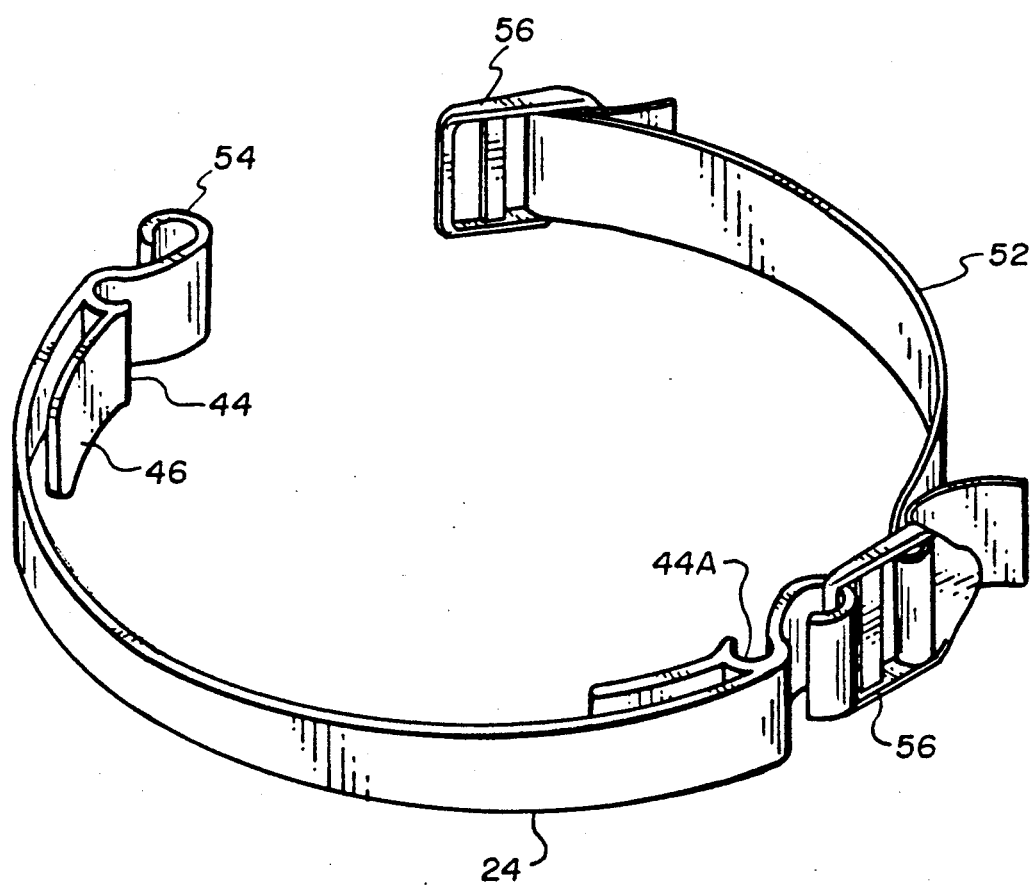
FIG. 5 depicts a cage member of the present invention with an adjustable strap for affixation around the user.

The cage members 24 grasp the support members 26, 28 by a latch means such as a notch, latch or jaw-like gripping portion 44, 44A placed on the ends of the cage members 24 (FIGS. 2, 4, & 5). The notch 44, 44A is of a diameter selected to grasp the support members 26, 28

(FIG. 6) or the wrapped end support members 26, 28 (FIGS. 2 & 4).

The effective diameter of the notch 44, 44A may be increased temporarily to grasp a cage member 24 to an support member 26 (FIG. 4). Such an increase is accomplished by the use of a lever or extension member 46 placed on the outer portion 48 of the notch or jaw 44. When the lever 46 is moved towards the cage member 24, the jaw or notch 44 pivots about pivot point 50 to open and thereby increases the effective diameter of the notch 44 (FIG. 4). Once released, the notch returns to its original diameter (FIG. 2) and firmly grasps the end support member or fabric-wrapped end support member 26.

To release the grasped end support member or fabric wrapped support member 26 (FIG. 4), the lever 46 is again moved to open the tensioned jaw-like grasping portion 44 thus increasing its diameter and releasing the grasped support member.

In the depicted embodiment, the jaw-like grasping portions 44, 44A are found on both ends of the cage members. In another embodiment (not shown), the cage member is permanently affixed to one support member, and encloses it allowing for at least partial rotation about that support member.

As shown in FIG. 3, a series of cage members (e.g. 24, 24A) are connected with the fabric wrapped support members 26, 28. The length of the support members 28, 30 and hence the number of cage members 24 are preferably chosen to protect the entire area of sensitive skin 38. The ladder-like apparatus 20 can thus be custom built for the particular user.

Straps 52, 52A or other affixation means typically wrap around the body portion 22 of the patient which has the area of sensitive skin (FIG. 1). The affixation means also connects to a portion of the apparatus, typically at least one of the cage members. If a strap is used, it can be elastic or otherwise adjustable in length.

The apparatus 20 depicted in FIG. 1 is affixed to the user by means of adjustable straps 52, 52A. These straps 52, 52A are connected to the apparatus 20 or cage members 24, and wrapped around the portion of the body of the user having the sensitive area of skin, e.g., the torso or a limb, 22.

The straps 52, 52A are preferably elastic or otherwise adjustable in length so as to affix the apparatus 20 firmly to the user. Alternatively, the apparatus can be affixed to the user with relatively loose straps while being affixed to the user by a belt assembly hung over a shoulder or around the waist of the user which suspends the apparatus in place (not shown).

When the straps are tightened about the user's body, the jaw like gripping portions of the lateral member grasps the support member with increased tension.

In the depicted embodiment, the straps 52, 52A are adapted to connect to the cage members 24 at their end(s). The hook arrangement 54 of the cage member 24 is adapted to connect to an eye, loop or buckle arrangement 56 connected to the strap 52.

In the buckle arrangement 56 shown (FIG. 2), the strap 52 can be adjusted in length to affix the apparatus firmly to the user. Furthermore, a strap 52 and associated buckle(s) can be removed from the apparatus 20 without removing the entire apparatus from the user. Also selectively chosen straps 52 can be wrapped around the user while others are left off for user comfort.

This "hook and eye" type arrangement allows the buckles and straps to be removed and replaced, but prevents them from becoming accidentally dislodged.

Preferably, a compressible foam pad 58 is placed in between the apparatus 20 and the user (FIG. 2). The foam pad 58 is preferably absorbent and preferably has one side with adhesive placed thereon for temporary affixation to the apparatus 20 or the user. Such foam pads are available from Wilshire Foam of Carson, Calif., and may be disposed of and replaced as needed.

The foam pad 58 has an aperture having a size similar to the aperture 42 of the fabric 40. The foam pad 58 adds to user comfort, and absorbs any liquids such as weeping fluids or excess topical preparations which may be present. The foam pad also helps to prevent the apparatus 20 from shifting onto the area of sensitive skin 38.

Figure 7:
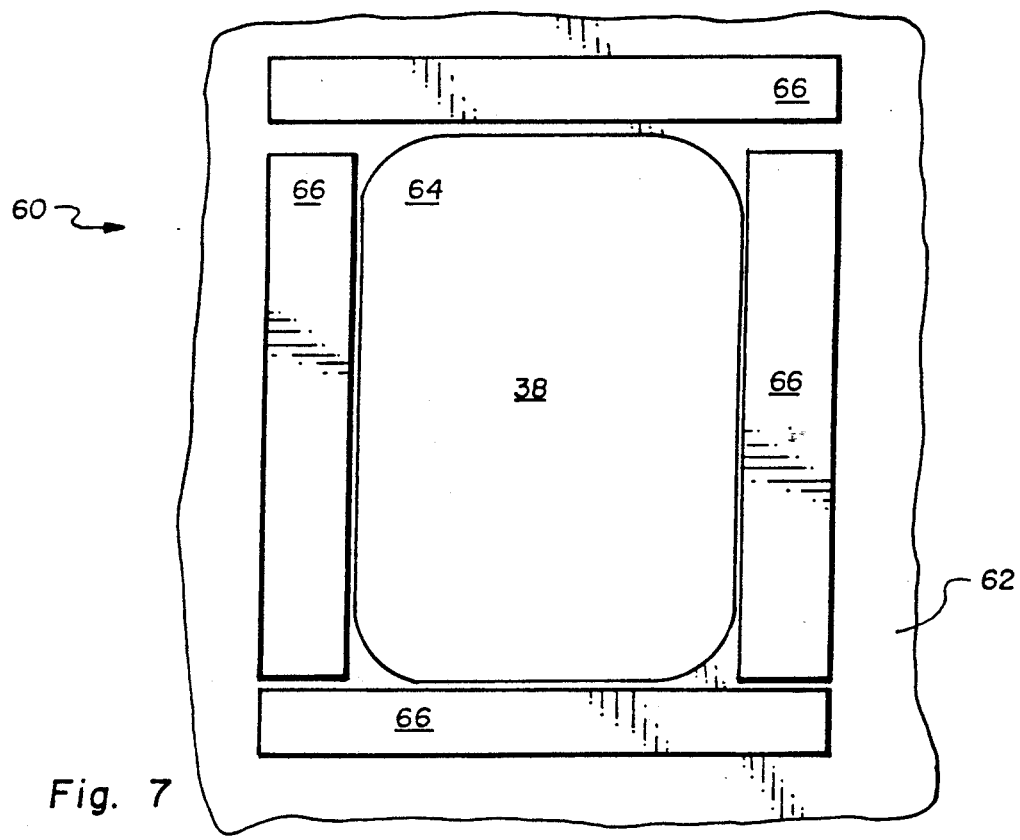
FIG. 7 depicts a representative type of pad for use in the present invention.

In the preferred embodiment, another pad is placed between the apparatus and the user, or the foam pad and the user, is a friction pad as depicted in FIG. 7. This mounting or friction pad 60, generally includes a net like portion 62 from which an aperture 64 has been cut or formed. Preferably the aperture 38 has a size slightly greater than that of the wound area and preferably surrounds the wound area without contacting it. An ideal material for use in the net-like portion is the Scoot-Gard ™ non-skid roll available from Vantage Industries, Inc. of Atlanta, Ga. This material is a loose-weaved polyester netting matrix coated with a soft polyvinyl chloride foam material which has been softened with the plasticizer dioctyl phthalate (DOP).

Pad 66 or pads may be sewn, glued, thermally bonded, or otherwise attached to the net-like portion around the perimeter of the aperture. Ideally, such a pad is absorbent, flexible and washable. The pad may also have an adhesive associated with it for adhesion to the apparatus, pad, or user. One absorbent pad found to work well with the friction pad is sold under the trade designation Poly-pad from Hermitage Hospital Products of Niantic, Conn.

The friction pad helps to prevent slippage of the skin guard apparatus, while its net-like structure still allows the skin to ventilate and the absorbent pad absorbs excess fluids.

Reference herein to specific details or certain embodiments is not intended to limit the scope of the appended claims.

What is claimed:

1. Apparatus for providing a ventilated shielding over a skin region of a user's body part, said apparatus comprising:

a pair of support members separated a distance from each other and adapted for approximately parallel placement from each other straddling said skin region;

a plurality of resilient arcuate cage members each having opposing ends connected to said support members, said cage members being arranged parallel and spaced from one another thereby defining air circulation passages between said cage members, said cage members being resiliently deformable springs having a relaxed condition wherein said members have a relaxed effective length which is greater than said distance and a compressed arched condition inducible by urging said opposing ends towards each other;

position maintenance means connecting said support members and extending adjacent said skin region for maintaining said support members in relative positions separated by said distance, thereby urging said opposing ends of said cage members toward each other and inducing said cage members to said compressed condition; and attachment means adapted to extend away from said cage members and encircle said user's body part for attaching said cage members to said user's body part above said skin region with said support members held against said user's body part.

2. The ventilated skin shielding apparatus of claim 1 wherein said position maintenance means is flexible and comprises a pair of straps, one strap fastened to an end of each of said support members, and the other strap fastened to the other end of each of said support members.

3. The ventilated skin shielding apparatus of claim 1 wherein said position maintenance means comprises a fabric panel with a central aperture configured to circumscribe said region.

4. The ventilated skin shielding apparatus of claim 1, wherein said attachment means further includes adjustment means for adjusting said attachment means to fit said user's body part.

5. The ventilated skin shielding apparatus of claim 4, wherein said attachment means comprises at least one strap having a first end connected to an end of one of said cage members, a second end, and buckle means connecting said second end to an opposite end of said cage member for adjusting the length of said strap.

6. The ventilated skin shielding apparatus of claim 1, further including latch means associated with at least one end of each said cage members for releasably connecting said cage members to said support members.

7. The ventilated skin shielding apparatus of claim 6, wherein said latch means is a normally closed resilient clasp having a lever movable to open said clasp to insert or remove one of said end support members therein.

8. The ventilated skin shielding apparatus of claim 7, wherein said cage member ends having said latch means further include connection means for interconnecting said cage member with said attachment means.

9. The ventilated skin shielding apparatus of claim 8, wherein said attachment means further includes adjustment means for adjusting said attachment means to fit said user's body part.

10. The ventilated skin shielding apparatus of claim 9 wherein said attachment means comprises at least one strap having a first end connected to an end of one of said cage members, a second end, and buckle means connecting said second end to an opposite end of said cage member for adjusting the length of said strap.

11. A ventilated skin shielding apparatus for protecting an area of damaged skin on a body part, comprising:
a pair of support members adapted for placement in approximately parallel spaced relationship to each other to straddle an area of damaged skin;
a plurality of resilient arcuate cage members each having opposing ends connected to said support members and latch means associated with at least one of said ends for releasably connecting said cage member to one of said support members, said cage members being disposed above said damaged skin and arranged parallel to one another in a spaced array defining air circulation passages between said cage members,
said latch means comprising a normally closed clasping jaw resiliently movable to an open position for placement or removal from one of said support members; and
attachment means associated with said cage member ends for affixing said support members against the skin of said body part.

12. The ventilated skin shielding apparatus of claim 11, wherein said latch means further includes a lever disposed for movement by a user to effect opening of said normally closed clasp.

13. The ventilated skin shielding apparatus of claim 11, wherein said cage member ends having said latch means further include connection means for interconnecting said cage member with said attachment means.

14. The ventilated skin shielding apparatus of claim 13, wherein said attachment means further includes adjustment means for adjusting said attachment means to fit said user's body part.

15. The ventilated skin shielding apparatus of claim 14 wherein said attachment means comprises at least one strap having a first end connected to an end of one of said cage members, a second end, and buckle means connecting said second end to an opposite end of said cage member for adjusting the length of said strap.

16. The ventilated skin shielding apparatus of claim 11, further including position maintenance means disposed below said cage members for holding said support members in said spaced relationship.

17. A protective cage member with associated connection elements for use in a skin protection apparatus having parallel spaced end support members connected by at least one attachment element extending around a user's body part to affix the skin protection apparatus thereto, comprising
a bowed elongate frame having two ends which are connectable to end support members, and at least one of said ends having
latch means associated thereto for releasably connecting said bowed elongate frame to and from an end support member, said latch means comprising a normally closed clasp which is resiliently movable to an open position for placement or removal of an end support member; and
connection means associated thereto for interconnecting said bowed elongate frame with an attachment element for affixing the skin protection apparatus to a user.

18. The protective cage member of claim 17, wherein each of said ends has said latch means and said connection means.

19. The protective cage member of claim 17, wherein said normally closed clasp has a lever formed thereon, said lever being movable to open said clasp to insert or remove an end support member.

20. The protective cage member of claim 19, wherein said connection means is a hook.

21. Apparatus for providing a ventilated shielding over a skin region of a user's body part, said apparatus comprising:
a pair of support members separated a distance from each other and adapted for approximately parallel placement from each other straddling said skin region, said support members being attached to each other by a material which at least partially circumscribes said region;
a plurality of resilient arcuate cage members each having opposing ends connected to said support members, said cage members being arranged parallel and spaced from one another thereby defining air circulation passages between said cage members, said cage members being resiliently deformable springs having a relaxed condition wherein said members have a relaxed effective length and a compressed condition inducible by urging said opposing ends towards each other, whereby the stiffness of said cage members is increased, and said material connecting said support members having a length which limits the distance between said support members to a distance less than said relaxed effective length of said cage members, thereby inducing said cage members to said compressed condition; and attachment means adapted to extend away from said cage members for holding said cage members above said region with said support members affixed against a user's body part.

22. Apparatus for providing a ventilated shielding over a skin region which is sensitive on a user's body part, said apparatus comprising:

a pair of support members separated a distance from each other and adapted for approximately parallel placement from each other straddling said skin region for connecting said support members to each other, sized to establish said distance between said support members, and arranged to avoid said skin region;

a plurality of resilient arcuate cage members each having opposing ends connected to said support members, said cage members being arranged parallel and spaced from one another, said cage members being resiliently deformable springs having a relaxed condition wherein said members have a relaxed effective length which is greater than said distance and a compressed condition inducible by urging said opposing ends towards each other to limit their separation to said distance; and attachment means adapted to extend away from said cage members for attaching said cage members to said user's body part above said region with said support members positioned against said user's body part.

* * * * *